(12) United States Patent
Lee et al.

(10) Patent No.: US 9,163,206 B2
(45) Date of Patent: Oct. 20, 2015

(54) CULTURE APPARATUS AND METHOD OF REPLACING CULTURE MEDIUM

(75) Inventors: Dong Woo Lee, Suwon (KR); Sang Jin Kim, Hwaseong (KR)

(73) Assignee: Samsung Electro-Mechanics Co., Ltd., Suwon-si (KR)

( * ) Notice: Subject to any disclaimer, the term of this patent is extended or adjusted under 35 U.S.C. 154(b) by 86 days.

(21) Appl. No.: 13/364,792

(22) Filed: Feb. 2, 2012

(65) Prior Publication Data

US 2013/0102068 A1    Apr. 25, 2013

(30) Foreign Application Priority Data

Oct. 25, 2011  (KR) .................. 10-2011-0109262

(51) Int. Cl.
| | |
|---|---|
| C12M 1/00 | (2006.01) |
| C12M 3/00 | (2006.01) |
| C12M 1/12 | (2006.01) |
| C12M 1/26 | (2006.01) |

(52) U.S. Cl.
CPC ............... *C12M 23/04* (2013.01); *C12M 29/00* (2013.01); *C12M 33/04* (2013.01); *Y10T 137/0318* (2015.04)

(58) Field of Classification Search
CPC ....... C12M 23/04; C12M 29/00; C12M 33/04
USPC ............................................. 435/283.1–309.4
See application file for complete search history.

(56) References Cited

U.S. PATENT DOCUMENTS

| | | | | |
|---|---|---|---|---|
| 2001/0021529 | A1* | 9/2001 | Takagi .......................... | 435/395 |
| 2006/0194193 | A1* | 8/2006 | Tsuruta et al. ................ | 435/4 |
| 2007/0248505 | A1* | 10/2007 | DeBruin ....................... | 422/131 |
| 2011/0111504 | A1* | 5/2011 | Knebel et al. ................ | 435/395 |

* cited by examiner

*Primary Examiner* — Nathan Bowers
*Assistant Examiner* — Lydia Edwards
(74) *Attorney, Agent, or Firm* — NSIP Law

(57) ABSTRACT

There is provided a culture apparatus including: a first pipe having a discharge channel formed at one end thereof; a second pipe having a suction channel formed at one end thereof; and a connection channel connecting the first and second pipes.

9 Claims, 7 Drawing Sheets

CULTURE APPARATUS AND METHOD OF REPLACING CULTURE MEDIUM

CROSS-REFERENCE TO RELATED APPLICATIONS

This application claims the priority of Korean Patent Application No. 10-2011-0109262 filed on Oct. 25, 2011, in the Korean Intellectual Property Office, the disclosure of which is incorporated herein by reference.

BACKGROUND OF THE INVENTION

1. Field of the Invention

The present invention relates to a culture apparatus and a method of replacing a culture medium, and more particularly, to a culture apparatus and a method of replacing a culture medium capable of continuously culturing cells or biomaterials.

2. Description of the Related Art

The demand for a biomedical apparatus and biotechnology for rapidly diagnosing various human diseases has recently increased. Therefore, the development for an experimentation apparatus and device capable of rapidly providing diagnostic results for a specific disease, tests for which have required a long period of time in a hospital or a research laboratory in the past, has been actively undertaken.

Meanwhile, in order to develop new medicines and to determine the experimental stability thereof, it is necessary to culture a cell. Cell culturing generally refers to injecting a cell and a cell culture medium into a culture vessel or a culture dish having a predetermined volume and culturing the cell and the cell culture for a predetermined time.

Here, in order to efficiently culture the cell, the culture medium should be replaced at a predetermined period. According to the related art, experimenters have automatically replaced the cell culture medium using a pump. However, since the pump and a pump control apparatus occupy a significant space, it may be difficult to simultaneously perform several culture medium replacement operations.

In addition, since an expensive pump and controller are required in the case of a scheme of replacing the culture medium using the pump, it is difficult to use the scheme in a small scale laboratory.

Therefore, the development of an experimentation apparatus or an experimentation device capable of replacing a fixed quantity of culture medium at a low cost has been urgently demanded.

SUMMARY OF THE INVENTION

An aspect of the present invention provides a culture apparatus capable of effectively replacing a culture medium without using a pump.

Another aspect of the present invention provides a method of replacing a culture medium capable of effectively replacing a culture medium using the culture apparatus.

According to an aspect of the present invention, there is provided a culture apparatus including: a first pipe having a discharge channel formed at one end thereof; a second pipe having a suction channel formed at one end thereof; and a connection channel connecting the first and second pipes.

The first pipe may be disposed in a position higher than that of the second pipe based on a direction of gravitational force.

The first pipe may have a water head larger than that of the second pipe.

The discharge channel may be extended in a direction perpendicular to a length direction of the first pipe.

The suction channel may be extended in a direction perpendicular to a length direction of the first pipe.

The connection channel may connect the other end of the first pipe and the other end of the second pipe to each other.

The other end of the first pipe and the other end of the second pipe may be open.

The culture apparatus may further include a closing member closing the other end of the first pipe and the other end of the second pipe.

The discharge channel and the suction channel may be disposed in parallel with each other.

The discharge channel may be disposed in a position higher than that of the suction channel based on a horizontal surface.

The first and second pipes may be formed integrally with each other.

The first pipe may be inclined with respect to the second pipe.

The first pipe may include a plurality of discharge channels.

The second pipe may include a plurality of suction channels.

Each of the first and second pipes may include a plurality of pipes disposed in parallel with each other.

According to another aspect of the present invention, there is provided a method of replacing a culture medium, the method including: a first operation of preparing a culture apparatus including a first pipe having a discharge channel formed at one end thereof, a second pipe having a suction channel formed at one end thereof, and a connection channel connecting the first and second pipes; a second operation of injecting the culture medium into the first pipe; a third operation of closing the other ends of the first and second pipes; a fourth operation of disposing the culture apparatus in a culture dish; and a fifth operation of opening the other ends of the first and second pipes.

The culture apparatus may be provided in plural, the plurality of culture apparatuses may be disposed in parallel with each other, and the first to fifth operations may be performed, in such a manner that a large quantity of the culture medium is simultaneously replaced.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE INVENTION

Hereinafter, embodiments of the present invention will be described in detail with reference to the accompanying drawings.

In describing the present invention below, terms indicating components of the present invention are named in consideration of functions of each component. Therefore, the terms should not be understood as being limited technical components of the present invention.

As described in the description of the related art, a culture medium needs to be replaced in order to efficiently culture a cell or a cell to which a new medicine is added. Generally, the culture medium has been manually replaced by an experimenter or automatically replaced by a motor or a control apparatus.

However, in the former case, since the experimenter should manually replace the culture medium, it may be difficult to replace a fixed quantity of culture medium. In the latter case unlike the former case, a fixed quantity of culture medium may be replaced; however, a space for installing the motor and the control apparatus is necessarily required and an expensive device should be purchased.

The present invention, provided to solve these defects, may provide a culture apparatus capable of replacing a fixed quantity of culture medium without using an expensive motor and control apparatus.

Figure 1:
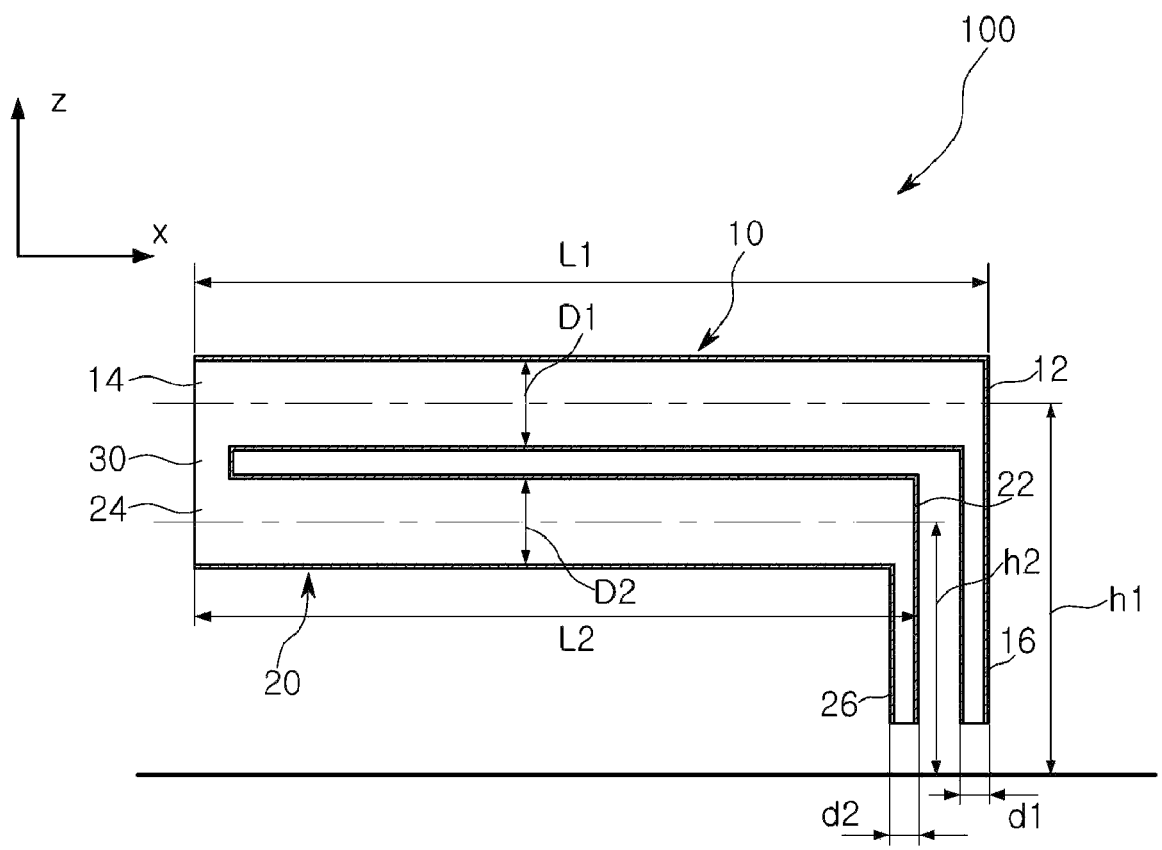
FIG. 1 is a cross-sectional view of a culture apparatus according to a first embodiment of the present invention.
Figure 2:
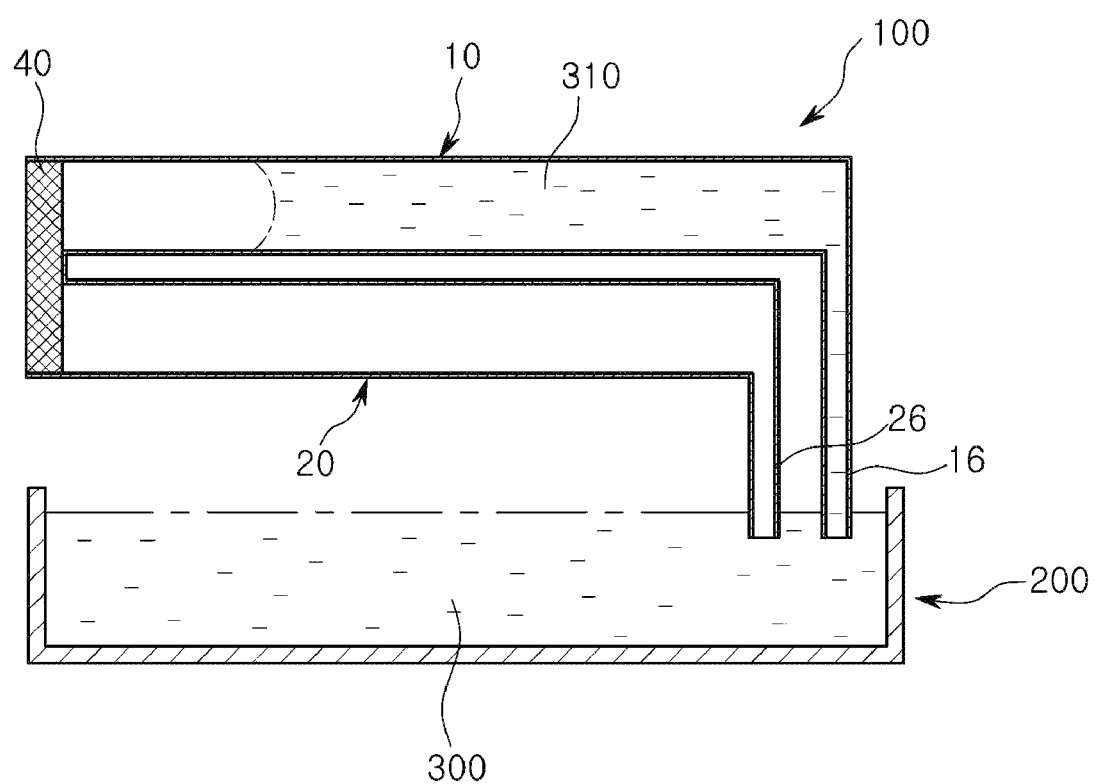
FIGS. 2 and 3 are cross-sectional views showing a state in which the culture apparatus shown in FIG. 1 is used.
Figure 3:
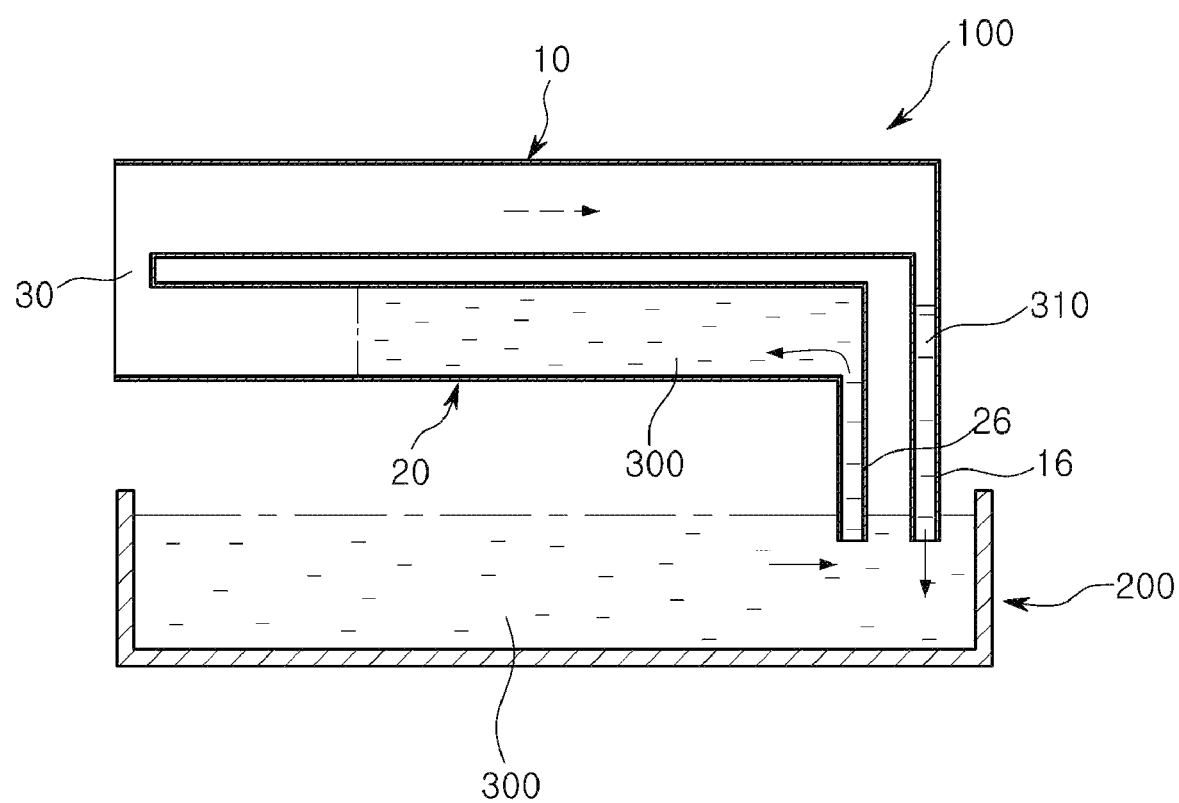
Figure 4:
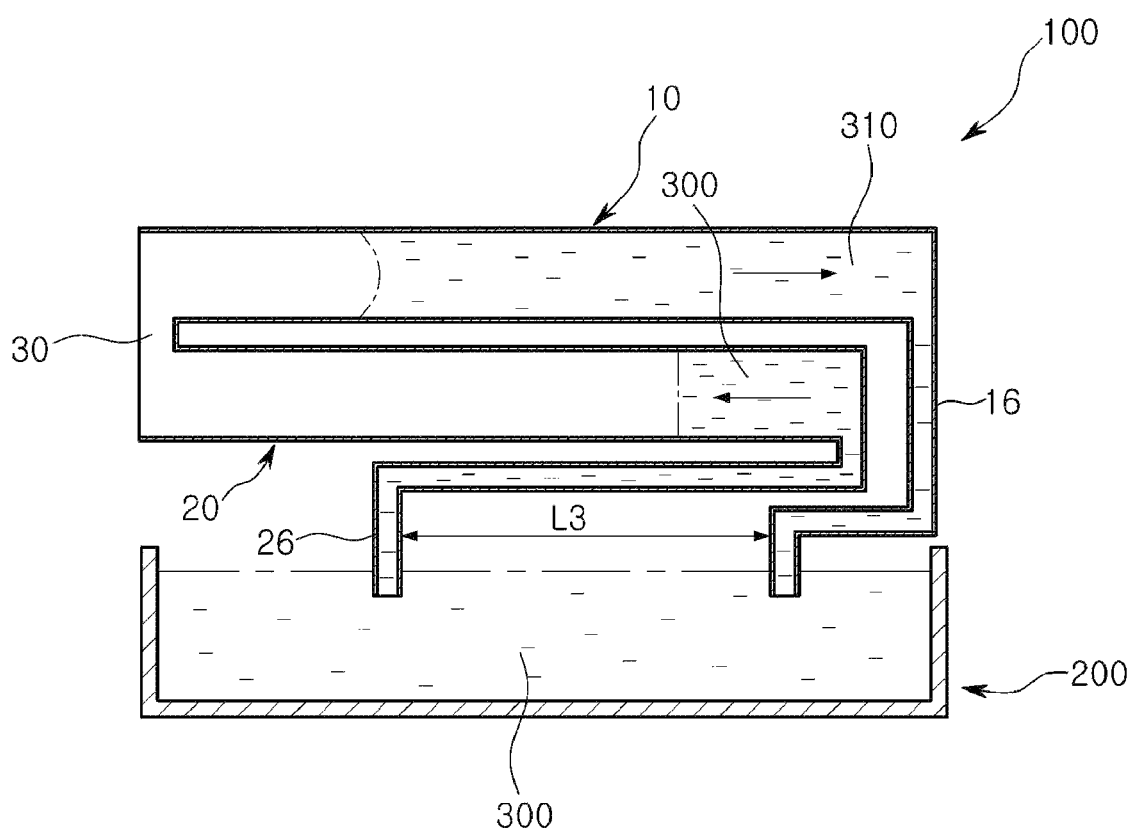
FIG. 4 is a cross-sectional view of a culture apparatus according to a second embodiment of the present invention.
Figure 5:
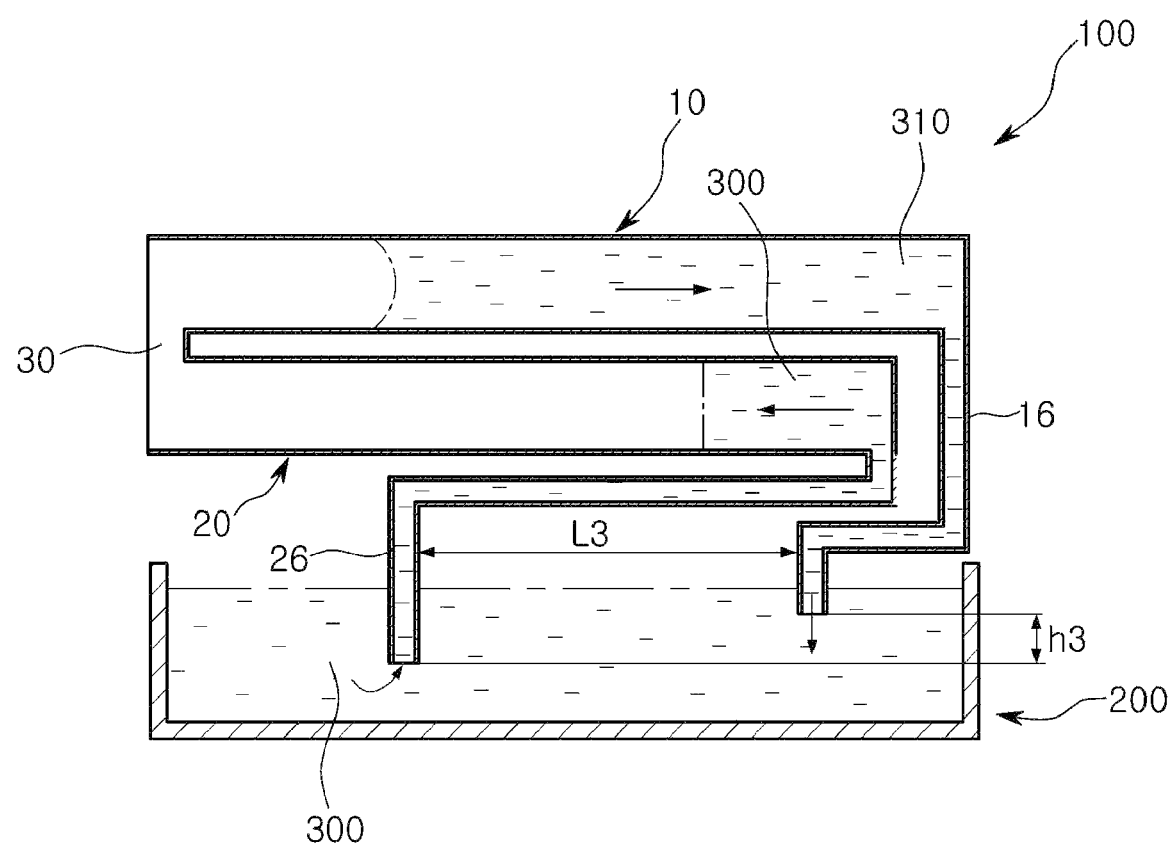
FIG. 5 is a cross-sectional view of a culture apparatus according to a third embodiment of the present invention.
Figure 6:
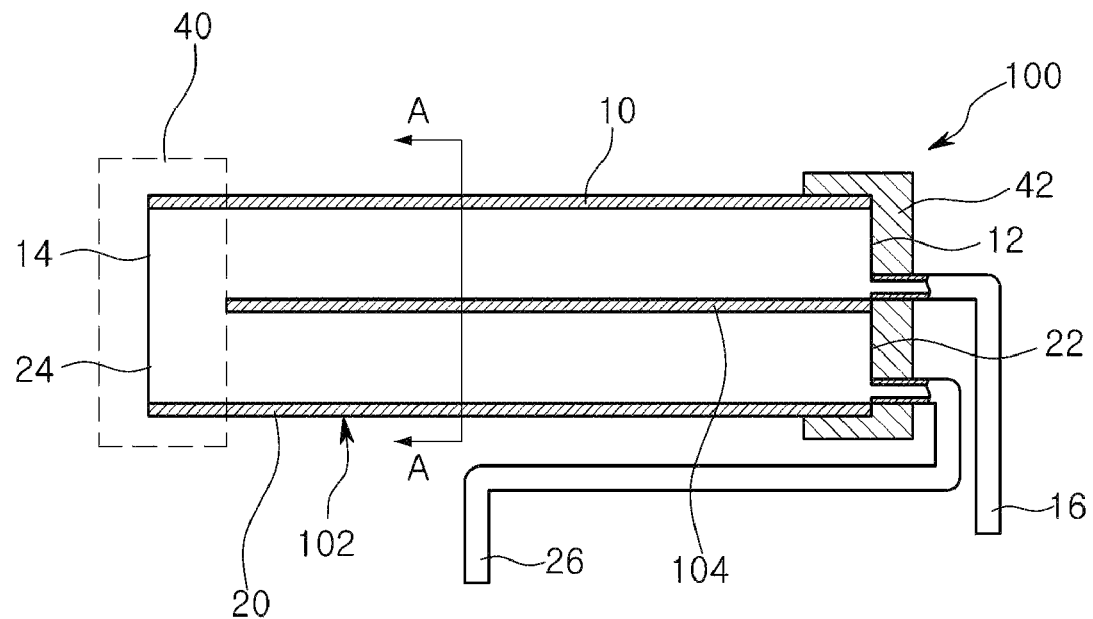
FIG. 6 is a cross-sectional view of a culture apparatus according to a fourth embodiment of the present invention.
Figure 7:
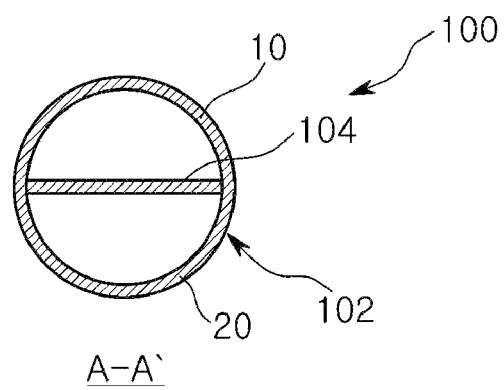
FIG. 7 is a cross-sectional view taken along line A-A of the culture apparatus shown in FIG. 6.
Figure 8:
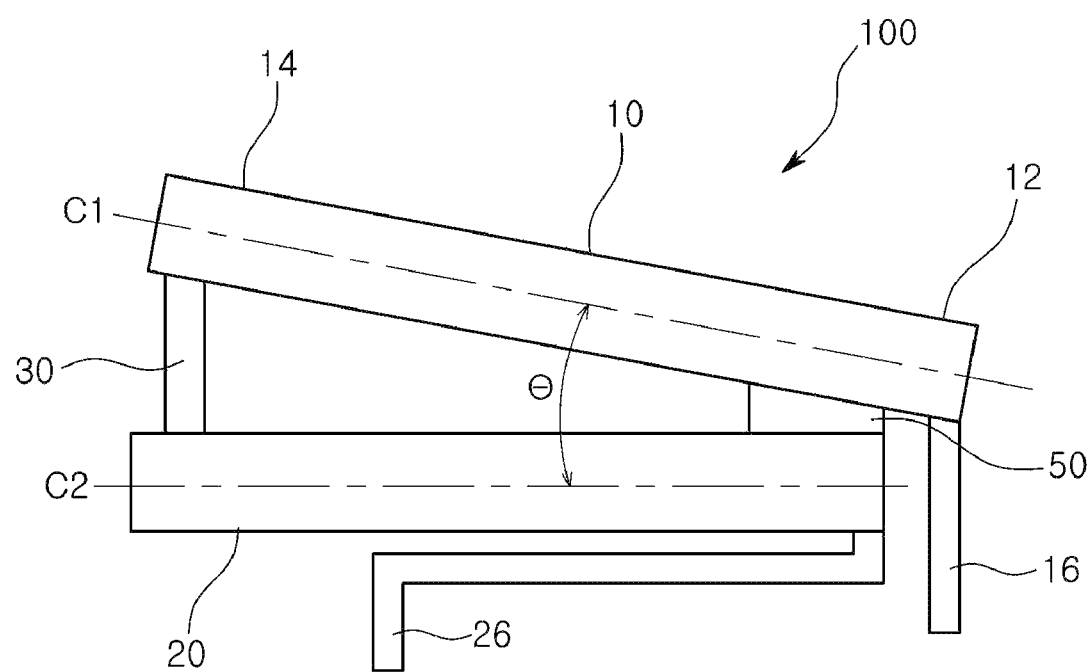
FIG. 8 is a cross-sectional view of a culture apparatus according to a fifth embodiment of the present invention.
Figure 9:
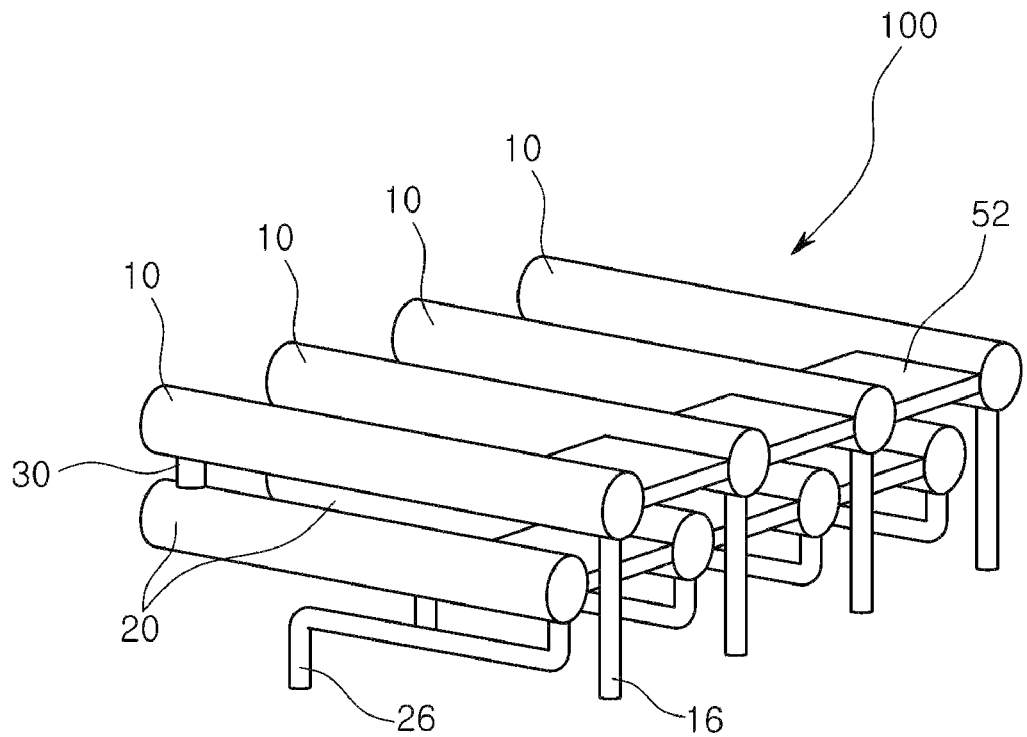
FIG. 9 is a cross-sectional view of a culture apparatus according to a six embodiment of the present invention.

FIG. 1 is a cross-sectional view of a culture apparatus according to a first embodiment of the present invention; FIGS. 2 and 3 are cross-sectional views showing a state in which the culture apparatus shown in FIG. 1 is used; FIG. 4 is a cross-sectional view of a culture apparatus according to a second embodiment of the present invention; FIG. 5 is a cross-sectional view of a culture apparatus according to a third embodiment of the present invention; FIG. 6 is a cross-sectional view of a culture apparatus according to a fourth embodiment of the present invention; FIG. 7 is a cross-sectional view taken along line A-A of the culture apparatus shown in FIG. 6; FIG. 8 is a cross-sectional view of a culture apparatus according to a fifth embodiment of the present invention; and FIG. 9 is a cross-sectional view of a culture apparatus according to a six embodiment of the present invention.

A culture apparatus according to a first embodiment of the present invention will be described with reference to FIGS. 1 through 3.

A culture apparatus according to the first embodiment of the present invention may include a first pipe 10, a second pipe 20, and a connection channel 30.

The first pipe 10 may generally have a circular shape. Specifically, the first pipe 10 may be a cylinder having a diameter of D1 and a length of L1. More specifically, the first pipe 10 may have a volume capable of storing a single injection of a culture medium therein.

The first pipe 10 may have a shape in which one end 12 or the other end 14 thereof is open. For reference, in the specification of the present invention, the first pipe 10 has a shape in which the other end 14 thereof is open. However, if needed, the first pipe 10 may have a shape in which one end 12 thereof is open and the other end 14 thereof is closed.

The first pipe 10 having the above-mentioned shape may store a second fluid 310, for example, a new medicine or a new culture medium (See FIG. 2), to be injected into a culture vessel or a culture dish 200 (See FIG. 2). For reference, when the second fluid 310 is injected into the first pipe 10, both of the other end 14 of the first pipe 10 and the other end 24 of the second pipe 20 may be closed by a finger of an experimenter or other closing members.

The first pipe 10 may include a discharge channel 16. The discharge channel 16 may be formed at one end 12 of the first pipe 10. However, in the case in which one end 12 of the first pipe 10 is open and the other end 14 thereof is closed, the discharge channel 16 may be formed at the other end 14 of the first pipe 10.

The discharge channel 16 may be extended downwardly (in a −Z axis direction based on FIG. 1) from the first pipe 10. Specifically, the discharge channel 16 may be extended to be long in a direction perpendicular to a length direction of the first pipe 10. In addition, an end of the discharge channel 16 may be disposed in a position (in the −Z direction based on FIG. 1) lower than that of the second pipe 20. The discharge channel 16 may have a cylindrical shape having a diameter of d1. Here, the diameter d1 of the discharge channel 16 may be smaller than a diameter D1 of the first pipe 10.

The discharge channel 16 having the above-mentioned shape may be used a path through which the second fluid 310 stored in the first pipe 10 is discharged to the culture dish 200.

The second pipe 20 may have a substantially circular shape. Specifically, the second pipe 20 may be a cylinder having a diameter of D2 and a length of L2. More specifically, the second pipe 20 may have a volume capable of storing a single amount of a culture medium to be collected therein. Here, the diameter D2 of the second pipe 20 may be equal to the diameter D1 of the first pipe 10, and the length L2 of the second pipe 20 may be equal to or smaller than the length L1 of the first pipe 10.

The second pipe 20 may have a shape in which one end 22 or the other end 24 thereof is open. For reference, in the specification of the present invention, the second pipe 20 has a shape in which the other end 24 thereof is open. However, if needed, the second pipe 20 may have a shape in which one end 22 thereof is open and the other end 24 thereof is closed.

The second pipe 20 having the above-mentioned shape may store a first fluid 300, for example, an old culture medium, received in the culture dish 200.

The second pipe 20 may include a suction channel 26. The suction channel 26 may be formed at one end 22 of the second pipe 20. However, in the case in which one end 22 of the second pipe 20 is open and the other end 24 thereof is closed, the suction channel 26 may be formed at the other end 24 of the second pipe 20.

The suction channel 26 may be extended downwardly (in the −Z axis direction based on FIG. 1) from the second pipe 20. Specifically, the suction channel 26 may be extended to be long in a direction perpendicular to a length direction of the second pipe 20. The suction channel 26 may have a cylindrical shape having a diameter of d2. Here, the diameter d2 of the suction channel 26 may be smaller than the diameter D2 of the second pipe 20 and be equal to the diameter d1 of the discharge channel 16. In addition, the suction channel 26 may be extended in parallel with the discharge channel 16 in the same direction as the direction in which the discharge channel 16 is extended.

The suction channel 26 having the above-mentioned shape may be used as a path for sucking the first fluid 300 received in the culture dish 200 into the second pipe 20

Meanwhile, the second pipe 20 may be disposed in parallel with the first pipe 10. More specifically, the second pipe 20 may be disposed in a position (in the −Z axis direction based on FIG. 1) lower than that of the first pipe 10 based on the direction in which the discharge channel 16 and the suction channel 26 are extended. Alternatively, the second pipe 20 may be disposed under the first pipe 10, while having a predetermined distance therebetween. Therefore, when it is assumed that the −Z axis direction is a direction of gravitational force, the fluid stored in the second pipe 20 may have a water head smaller than that of the fluid stored in the first pipe 10. That is, the fluid stored in the first pipe 10 may have a water head of h1 based on a virtual horizontal surface, and the fluid stored in the second pipe 20 may have a water head of h2 based on the virtual horizontal surface.

The connection channel 30 may allow the first and second pipes 10 and 20 to be in communication with each other. Specifically, the connection channel 30 may allow the other end 14 of the first pipe 10 and the other end 24 of the second pipe 20 to be in communication with each other. Therefore, gas or the fluid stored within the first pipe 10 may move into the second pipe 20 through the connection channel 30.

Hereinafter, a method of replacing a culture medium using the culture apparatus 100 configured as described will be described with reference to FIGS. 2 and 3.

The method of replacing a culture medium according to the embodiment of the present invention may include an operation of injecting a culture medium, an operation of closing pipes 10 and 20, an operation of disposing a culture apparatus 100, and an operation of opening the pipes 10 and 20.

(Culture Medium Injecting Operation)

The operation may be an operation of injecting the second fluid 310 into the first pipe 10. Here, the second fluid 301 may be a culture medium to be replaced in the first pipe 10 or a new medicine or other medicines to be injected into the culture dish 200.

The operation may be performed in a state in which the discharge channel 16 is closed so that the second fluid 310 is not discharged through the discharge channel 16. In addition, the operation may be performed in a state in which the first pipe 10 stands up in a direction in parallel with a direction of gravitational force so that the second fluid 310 is not discharged through the other end 14 of the first pipe 10.

(Pipe Closing Operation)

The operation may be an operation of closing the other end 14 of the first pipe 10 and the other end 24 of the second pipe 20. Alternatively, the operation may be an operation of closing the other end 14 of the first pipe 10 and the connection channel 30. Alternatively, the operation may include all operations of taking an action such that internal pressure of the first pipe 10 becomes lower than atmospheric pressure.

The other end 14 of the first pipe 10 and the other end 24 of the second pipe 20 may be closed by a separate closing member 40 as shown in FIG. 2. Here, the closing member 40 may be inserted into the other end 14 of the first pipe 10 and the other end 24 of the second pipe 20. The closing member 40 may also close the connection channel 30 allowing the other end 14 of the first pipe 10 and the other end 24 of the second pipe 20 to be in communication with each other.

When the other end 14 of the first pipe 10 and the other end 24 of the second pipe 20 are closed as described above, since the internal pressure of the first pipe 10 may becomes lower than the atmospheric pressure, even in the case in which the discharge channel 16 is open, the second fluid 310 injected into the first pipe 10 may not be discharged through the discharge channel 16.

Therefore, when the operation is performed, even in a state in which the second fluid 310 is filled in the first pipe 10, the culture apparatus 100 may be easily carried or disposed.

(Culture Apparatus Disposing Operation)

The operation may be an operation of disposing the culture apparatus 100 in the culture dish 200.

In the operation, the culture apparatus 100 may be disposed so that both of the discharge channel 16 and the suction channel 26 may be immersed in the first fluid 300 of the culture dish 200. Here, since both of the discharge channel 16 and the suction channel 26 are maintained in an open state, the first fluid 300 or the second fluid 310 may move through these channels 16 and 26.

(Pipe Opening Operation)

The operation may be an operation of opening the other end 14 of the first pipe 10 and the other end 24 of the second pipe 20. That is, the operation may be an operation of removing the closing member 40.

When the closing member 40 is removed in a state shown in FIG. 2, pressure at the other end 14 of the first pipe 10 and the other end 24 of the second pipe 20 may become the same as the atmospheric pressure. In this case, since the atmospheric pressure is applied to the second fluid 310 stored in the first pipe 10, the second fluid 310 of the first pipe 10 may be discharged to the culture dish 200 through the discharge channel 16.

Here, the fluid (that is, gas) stored in the second pipe 20 moves to the first pipe 10 through the connection channel 30 so as to be filled in an internal space of the first pipe 10, internal pressure of the second pipe 20 may become lower than the atmospheric pressure. In this case, the first fluid 300 of the culture dish 200 may move to the second pipe 20 through the suction channel 26 in order to compensate for pressure loss of the second pipe 20.

Therefore, according to the present embodiment, a process in which the second fluid 310 of the first pipe 10 is introduced into the culture dish 200 and a process in which the second fluid 300 of the culture dish 200 is introduced into the second pipe 20 may be simultaneously performed.

In the culture apparatus according to the embodiment configured as described above, a fixed quantity of fluid (that is, a culture medium) may be replaced without using a separate driving apparatus. Therefore, the culture apparatus according to the embodiment may be efficiently used in a small scale laboratory.

For reference, the operations of closing and opening pipes among the operations may be omitted. That is, after the culture medium is injected, the operation of disposing the culture apparatus is performed in a state in which a small quantity of culture medium flows, whereby the culture medium may be immediately performed.

Hereinafter, other embodiments of the present embodiment will be described. For reference, in the following embodiments, the same reference numerals will be used to describe the same components as those of the first embodiment. In addition, a detailed description of these components will be omitted.

Hereinafter, a culture apparatus according to a second embodiment of the present invention will be described with reference to FIG. 4.

The culture apparatus 100 according to the second embodiment of the present invention may be different from the culture apparatus according to the first embodiment of the present invention in that an end of the discharge channel 16 and an end of the suction channel 26 are disposed, while having a distance L3 therebetween. That is, the culture apparatus 100 according to the present embodiment is characterized in that the discharge channel 16 and the suction channel 26 are spaced apart from each other so that the second fluid 310 discharged through the discharge channel 16 is not sucked through the suction channel 26.

Here, the spaced distance L3 between the discharge channel 16 and the suction channel 26 may be changed according to a quantity of the second fluid 310 stored in the first pipe 10 or a size of the culture dish 200.

Hereinafter, a culture apparatus according to a third embodiment of the present invention will be described with reference to FIG. 5.

The culture apparatus 100 according to the third embodiment of the present invention may be different from the culture apparatuses according to the above-mentioned embodiments of the present invention in that an end of the discharge channel 16 and an end of the suction channel 26 are disposed in different heights.

According to the embodiment, the end of the discharge channel 16 and the end of the suction channel 26 are disposed to have a predetermined height difference h3 therebetween, such that the second fluid 310 supplied to the discharge channel 16 is not sucked through the suction channel 26.

Meanwhile, although the embodiment shows that the end of the discharge channel 16 is disposed in a position higher than that of the end of the suction channel 26, the end of the discharge channel 16 may be disposed in a position lower than that of the end of the suction channel 26 according to physical properties (specific gravity, viscosity, and the like) of the replaced or injected second fluid 310.

Hereinafter, a culture apparatus according to a fourth embodiment of the present invention will be described with reference to FIGS. 6 and 7.

The culture apparatus 100 according to the fourth embodiment of the present invention may be different from the culture apparatuses according to the above-mentioned embodiments of the present invention in that the first pipe 10 and the second pipe 20 are formed integrally with each other.

That is, in the culture apparatus 100 according to the fourth embodiment of the present invention, as shown in FIGS. 6 and 7, the first and second pipes 10 and 20 may be divided by forming a partition 104 in a single cylindrical member 102. Here, the partition 104 may have a length shorter than those of the pipes 10 and 20 so that the other end 14 of the first pipe 10 and the other end 24 of the second pipe 20 may be in communication with each other.

In addition, each of the discharge channel 16 and the suction channel 26 according to the fourth embodiment of the present invention may be detachable from the first and second pipes 10 and 20. That is, each of the discharge channel 16 and the suction channel 26 according to the fourth embodiment of the present invention may be inserted into an auxiliary closing member 42 coupled to one end of the first and second pipes 10 and 20 as shown in FIG. 6.

In the culture apparatus according to the embodiment configured as described above, since the pipes 10 and 20 and the channels 16 and 26 may be individually manufactured, the culture apparatus 100 may be easily manufactured.

Hereinafter, a culture apparatus according to a fifth embodiment of the present invention will be described with reference to FIG. 8.

The culture apparatus 100 according to the fifth embodiment of the present invention may be different from the culture apparatuses according to the above-mentioned embodiments of the present invention in that the first pipe 10 is disposed to be inclined with respect to the second pipe 20.

That is, according to the present embodiment, a first axis C1 penetrating through the first pipe 10 and a second axis C2 penetrating through the second pipe 20 may form a predetermined angle θ. Specifically, the other end 14 of the first pipe 10 may be disposed in a position higher than that of one end 12 thereof so that the fluid of the first pipe 10 may be smoothly discharged through the discharge channel 16.

In addition, the culture apparatus 100 according to the present embodiment may further include a first connection member 50 so that a disposition shape of the first and second pipes 10 and 20 may be maintained.

Hereinafter, a culture apparatus according to a sixth embodiment of the present invention will be described with reference to FIG. 9.

The culture apparatus 100 according to the sixth embodiment of the present invention may be different from the culture apparatuses according to the above-mentioned embodiments of the present invention in that the first pipe 10 and the second pipe 20 are provided in plural, the plurality of first pipes 10 are disposed in parallel with each other and the plurality of second pipes 20 are also disposed in parallel with each other as shown in FIG. 9. That is, the respective first pipes 10 may be connected to each other by a second connection member 52, while having a predetermined interval therebetween, and the respective second pipes 20 may be connected to each other by the second connection member 52, while having a predetermined interval therebetween.

In the culture apparatus according to the embodiment configured as described above may be usefully used to replace a large quantity of culture medium or simultaneously replace culture mediums of the culture dishes 200 disposed at predetermined intervals.

As set forth above, according to embodiments of the present invention, a pump is not used, such that a large space is not required to replace a culture medium.

In addition, a culture apparatus according to the embodiments of the present invention does not require an expensive fixed-quantity pump and a controller, such that the culture apparatus may be used in a small scale laboratory or a university laboratory.

Further, according to the embodiments of the present invention, a plurality of culture apparatuses are disposed and used in parallel with each other, whereby several culture medium replacing operations may be simultaneously performed.

While the present invention has been shown and described in connection with the embodiments, it will be apparent to those skilled in the art that modifications and variations can be made without departing from the spirit and scope of the invention as defined by the appended claims.

What is claimed is:

1. A culture apparatus comprising:
   a first pipe having a discharge channel formed at one end thereof and immersed in a culture dish;
   a second pipe having a suction channel formed at one end thereof and immersed in the culture dish;
   a connection channel connecting the first pipe and the second pipe,
   wherein:
   the first pipe is disposed in a position higher than that of the second pipe based on the connection channel,
   the first pipe and the second pipe are extended in the same direction,
   the discharge channel is extended in a direction perpendicular to a length direction of the first pipe,
   the suction channel is extended in a direction perpendicular to a length direction of the first pipe,
   the discharge channel, the suction channel, and the connection channel are disposed in parallel with each other,
   the other end of the first pipe and the other end of the second pipe are open, and the culture apparatus further comprises a closing member plugging the other end of the first pipe and the other end of the second pipe.

2. The culture apparatus of claim 1, wherein the first pipe is disposed in a position higher than that of the second pipe based on a direction of gravitational force.

3. The culture apparatus of claim 1, wherein the first pipe has a water head larger than that of the second pipe.

4. The culture apparatus of claim 1, wherein the connection channel connects the other end of the first pipe and the other end of the second pipe to each other.

5. The culture apparatus of claim 1, wherein the discharge channel is disposed in a position higher than that of the suction channel based on a horizontal surface.

6. The culture apparatus of claim 1, wherein the first and second pipes are formed integrally with each other.

7. The culture apparatus of claim 1, wherein the first pipe includes a plurality of discharge channels.

8. The culture apparatus of claim 1, wherein the second pipe includes a plurality of suction channels.

9. The culture apparatus of claim 1, wherein each of the first and second pipes includes a plurality of pipes disposed in parallel with each other.

\* \* \* \* \*